United States Patent
Hofmann et al.

(10) Patent No.: US 11,266,424 B2
(45) Date of Patent: Mar. 8, 2022

(54) AUTONOMOUS CATHETERIZATION ASSEMBLY

(71) Applicant: Siemens Healthcare GmbH, Erlangen (DE)

(72) Inventors: Bernd Hofmann, Erlangen (DE); Friedrich Fuchs, Hessdorf (DE); Erin Girard, New York, NY (US)

(73) Assignee: Siemens Healthcare GmbH, Erlangen (DE)

( * ) Notice: Subject to any disclaimer, the term of this patent is extended or adjusted under 35 U.S.C. 154(b) by 383 days.

(21) Appl. No.: 16/006,978

(22) Filed: Jun. 13, 2018

(65) Prior Publication Data
US 2018/0360479 A1    Dec. 20, 2018

(30) Foreign Application Priority Data
Jun. 20, 2017    (EP) .................................... 17176754

(51) Int. Cl.
*A61B 17/22*    (2006.01)
*A61B 34/20*    (2016.01)
(Continued)

(52) U.S. Cl.
CPC .............. *A61B 17/22* (2013.01); *A61B 34/20* (2016.02); *A61B 34/30* (2016.02);
(Continued)

(58) Field of Classification Search
CPC .......... A61B 17/22; A61B 2017/22042; A61B 2017/22071; A61B 2017/00022;
(Continued)

(56) References Cited

U.S. PATENT DOCUMENTS

| | | | |
|---|---|---|---|
| 5,423,846 | A | 6/1995 | Fischell |
| 5,492,131 | A | 2/1996 | Galel |

(Continued)

FOREIGN PATENT DOCUMENTS

| | | |
|---|---|---|
| CN | 2208422 Y | 9/1995 |
| CN | 101612436 A | 12/2009 |

(Continued)

OTHER PUBLICATIONS

German Office Action for German Application No. 17176754.4-1124 dated Mar. 1, 2018.

(Continued)

*Primary Examiner* — Anh T Dang
(74) *Attorney, Agent, or Firm* — Harness, Dickey & Pierce, P.L.C.

(57) ABSTRACT

An autonomous catheterization assembly includes a catheter arrangement for insertion into the vascular system of a patient. In an embodiment, the catheter arrangement includes a sensor arrangement to sense a condition in the interior of a vessel of the vascular system, a shape adjustment device arranged in a distal portion of the catheter arrangement, and an actuator arrangement to control the shape adjustment device to adjust the shape and/or orientation of the distal portion of the catheter arrangement. The autonomous catheterization assembly further includes a propulsion assembly to propel elements of the catheter arrangement through the vascular system of the patient; a route computation module to compute a route through the vascular system to a target; and a control unit to actuate the propulsion assembly based upon the computed route and/or in response to a sensed condition in the interior of a vessel of the vascular system.

12 Claims, 3 Drawing Sheets

(51) Int. Cl.
A61M 25/01 (2006.01)
A61B 34/30 (2016.01)
A61B 17/00 (2006.01)
A61F 2/95 (2013.01)
A61B 5/0215 (2006.01)
A61B 90/00 (2016.01)
A61B 17/3207 (2006.01)
A61B 90/30 (2016.01)

(52) U.S. Cl.
CPC ........ *A61M 25/0116* (2013.01); *A61B 5/0215* (2013.01); *A61B 17/3207* (2013.01); *A61B 2017/00022* (2013.01); *A61B 2017/22042* (2013.01); *A61B 2017/22071* (2013.01); *A61B 2034/2051* (2016.02); *A61B 2034/2055* (2016.02); *A61B 2034/2059* (2016.02); *A61B 2034/2065* (2016.02); *A61B 2034/301* (2016.02); *A61B 2090/061* (2016.02); *A61B 2090/065* (2016.02); *A61B 2090/309* (2016.02); *A61B 2090/376* (2016.02); *A61B 2090/3735* (2016.02); *A61B 2090/3966* (2016.02); *A61F 2/95* (2013.01); *A61F 2002/9528* (2013.01); *A61M 2205/3334* (2013.01)

(58) Field of Classification Search
CPC .............. A61B 34/20; A61B 2090/061; A61B 2034/2059; A61B 2034/301; A61M 25/0116
See application file for complete search history.

(56) References Cited

U.S. PATENT DOCUMENTS

| | | | |
|---|---|---|---|
| 7,615,042 | B2 | 11/2009 | Beyar et al. |
| 7,803,169 | B2 | 9/2010 | Shamay |
| 8,046,049 | B2 | 10/2011 | Govari et al. |
| 8,694,157 | B2 | 4/2014 | Wenderow et al. |
| 9,220,568 | B2 | 12/2015 | Bromander et al. |
| 9,510,912 | B2 | 12/2016 | Bencteux et al. |
| 9,827,047 | B2 | 11/2017 | Fudaba et al. |
| 10,238,456 | B2 | 3/2019 | Murphy et al. |
| 2005/0004579 | A1 | 1/2005 | Schneider et al. |
| 2008/0140101 | A1 | 6/2008 | Carley et al. |
| 2011/0152882 | A1* | 6/2011 | Wenderow ............. A61B 34/37 606/130 |
| 2012/0179032 | A1 | 7/2012 | Bromander et al. |
| 2012/0271319 | A1 | 10/2012 | Bromander et al. |
| 2014/0142594 | A1 | 5/2014 | Fojtik |
| 2014/0276939 | A1 | 9/2014 | Kokish et al. |
| 2015/0029864 | A1 | 1/2015 | Raileanu et al. |
| 2015/0057575 | A1 | 2/2015 | Tsusaka et al. |
| 2015/0105747 | A1 | 4/2015 | Rollins et al. |
| 2015/0148816 | A1 | 5/2015 | Govari et al. |
| 2017/0071684 | A1 | 3/2017 | Kokish et al. |
| 2017/0151024 | A1 | 6/2017 | Deboeuf et al. |

FOREIGN PATENT DOCUMENTS

| | | |
|---|---|---|
| CN | 102028549 B | 6/2012 |
| CN | 103157170 A | 6/2013 |
| CN | 103584918 A | 2/2014 |
| CN | 103083783 B | 7/2014 |
| CN | 103976766 A | 8/2014 |
| CN | 104667412 A | 6/2015 |
| DE | 20017949 U1 | 11/2001 |
| DE | 102004007935 A1 | 5/2005 |
| DE | 102005042326 A1 | 3/2007 |
| DE | 102011107614 A1 | 1/2013 |
| EP | 1566150 A2 | 8/2005 |
| EP | 1732437 B1 | 1/2012 |
| EP | 2626033 B1 | 3/2018 |
| FR | 2893851 A1 | 6/2007 |
| FR | 2979532 A1 | 3/2013 |
| FR | 3016512 A1 | 7/2015 |
| JP | H0531117 A | 2/1993 |
| JP | 2005-103018 A | 4/2005 |
| JP | 2006-167298 A | 6/2006 |
| JP | 2015-100708 A | 6/2015 |
| JP | 2015-535195 A | 12/2015 |
| WO | WO-9744089 A1 | 11/1997 |
| WO | WO-2011/018147 A1 | 2/2011 |
| WO | WO-2011/018157 A1 | 2/2011 |
| WO | WO-2014/074955 A1 | 5/2014 |
| WO | WO-2014/127353 A1 | 8/2014 |
| WO | WO-2014/135813 A1 | 9/2014 |
| WO | WO-2014/135814 A1 | 9/2014 |
| WO | WO-2015/197996 A1 | 12/2015 |
| WO | WO-2018/078568 A1 | 5/2018 |
| WO | WO-2018/165162 A1 | 9/2018 |
| WO | WO-2019/133438 A1 | 7/2019 |

OTHER PUBLICATIONS

Guo, S. et al. "A Novel Active Catheter System for Ileus Treatment." Proceedings of the IEEE International Conference on Automation and Logistics (Sep. 2008): pp. 67-72.

"Application of rotating catheter in different catheterization." *Chinese Community Doctors*, No. 14 (2010).

Wang, D. et al. "Toward In-Vivo Force and Motion Measurement for Vascular Surgery." *IEEE Transactions on Instrumentation and Measurement* (Aug. 2014).

Liu, D. "Vascular Interventional Surgery Robot Motion Planning and Catheter Navigator Design." Dissertation Submitted for the Degree of Master, School of Mechanical Engineering & Automation, Beihang University, Beijing, China (2011).

Arai, F. et al. "New Catheter Driving Method Using Linear Stepping Mechanism for Intravascular Neurosurgery." Proceedings of the 2002 IEEE International Conference on Robotics & Automation (May 2002): pp. 2944-2949.

Azizian, M. et al. "Image Processing Algorithms for Real-Time Tracking and Control of an Active Catheter." 2007 European Control Conference (ECC) (2007): 2135-2142.

Bertocchi, U. et al. "Human-Robot Shared Control for Robot-Assisted Endoscopy of the Spinal Cord." The First IEEE/RAS-EMBS International Conference on Biomedical Robotics and Biomechatronics (2006): 543-548.

Beyar, R. et al. "Remote-Control Percutaneous Coronary Interventions: Concept, Validation, and First-in-Humans Pilot Clinical Trial." *Journal of the American College of Cardiology* 47:2 (2006): 296-300.

Chen, Y. "Multi-turn, Tension-stiffening Catheter Navigation System." 2010 IEEE International Conference on Robotics and Automation (May 2010): 5570-5575.

Comber, D.G. et al. "Open-Loop Tip Accuracy of an MRI-Compatible Active Cannula Robot." Proceedings of the Hamlyn Symposium on Medical Robotics (2013): 112-113.

Feng, Z.Q. et al. "Design and Evaluation of a Bio-inspired Robotic Hand for Percutaneous Coronary Intervention." 2015 IEEE International Conference on Robotics and Automation (ICRA) (2015).

Fu, Y. et al. "The master-slave catheterisation system for positioning the steerable catheter." *Int. J. Mechatronics and Automation* 1:3/4 (2011): 143-152.

Ganji, Y. "A Platform for Robot-Assisted Intracardiac Catheter Navigation." Thesis presented to the University of Waterloo in fulfillment of the thesis requirement for the degree of Doctor of Philosophy in electrical and Computer Engineering (2009).

Gao, B. et al. "Design of the Virtual Reality based Robotic Catheter System for Minimally Invasive Surgery Training." Proceeding of the IEEE International Conference on Automation and Logistics (Aug. 2012): 622-627.

Huang, SKS et al. (ed.) *Catheter Ablation of Cardiac Arrythmias* (2014): 154-155.

Huang, J. "A New Catheter Driving Device for Endovascular and Neurovascular Surgery." Masters Thesis; Graduate School of the University at Buffalo, State University of New Department of (56) References Cited

OTHER PUBLICATIONS

Mechanical and Aerospace Engineering (2013).

Jayender, J. et al. "Autonomous Robot-Assisted Active Catheter Insertion using Image Guidance." Proceedings of the 2007 IEEE/RSJ International Conference on Intelligent Robots and Systems (2007): 889-894.

Ji, C. et al. "Guidewire Navigation and Delivery System for Robot-Assisted Cardiology Interventions." IEEE 10th International Conference on Cognitive Informatics and Cognitive Computing (2011): 330-335.

Kanagaratnam, P. et al. "Experience of robotic catheter ablation in humans using a novel remotely steerable catheter sheath." *J. Interv. Card. Electrophysiol.* 21 (2008): 19-26.

Kesner, S.B. and R. Howe. "Force Control of Flexible Catheter Robots for Beating Heart Surgery." *IEEE Int Conf Robot Autom* (2011): 1589-1594.

Kesner, S.B. et al. "Ultrasound Servoing of Catheters for Beating Heart Valve Repair." International Conference on Information Processing in Computer-Assisted Interventions (2010): 168-178.

Kesner, S.B. "Robotic Catheters for Beating Heart Surgery." Ph.D. Dissertation; The Harvard School of Engineering and Applied Sciences (Dec. 2011).

Loschak, P.M. "Automated Pointing of Cardiac Imaging Catheters." *IEEE Int Conf Robot Autom.* (2013): 5794-5799.

Moon, Y. et al. "A Tele-operated Robotic Platform for Cardiovascular Catheter Intervention With Haptic Guidance." *14th International Conference on Control, Automation and Systems (ICCAS)* (2014).

Nölker, G et al. "Novel Robotic Catheter Manipulation System Integrated With Remote Magnetic Navigation for Fully Remote Ablation of Atrial Tachyarrhythmias: a Two-centre Evaluation." *Europace* 14(12) (2012): 1715-1718.

Perrino, A.C. et al. *Practical Approach to Transesophageal Echocardiography.* Chapter 2, "Two-dimensional examination." (2013).

Qi, P et al. "Towards Kinematic Modeling of a Multi-dof Tendon Driven Robotic Catheter." *Annual International conference of the IEEE Engineering in Medical and Science 2014* (2014): 3009-3012.

Saliba, W et al. "Atrial Fibrillation Ablation Using a Robotic Catheter Remote Control System." *Journal of the American College of Cardiology* 51 (25) (2008): 2407-2411.

Smoljkic, G et al. "Towards Intraoperative Use of Surgical Simulators: Evaluation of Catheter Insertion Models." *Proceedings of 3rd Joint Workshop on New Technologies for Computer/Robot Assisted Surgery (CRAS) 2013* (2013): 45-47.

Snow, N. "Elimination of Lead Dislodgement by the Use of Tined Transvenous Electrodes." *PACE* vol. 5 (1982): 571-574.

Erglis, A. et al. "Tools & Techniques: coronary guidewires." *EuroIntervention* vol. 6 (2010): 1-8.

Tran, P.T. et al. "Patient-specific Design of Multi-component Steerable Catheters." *Proceedings of the 3rd Joint Workshop on New Technologies for Computer/Robot Assisted Surgery 2013* (2013): 37-40.

Wang, JQ et al. "Computer-assisted Navigation Systems for Insertion of Cannulated Screws in Femoral Neck Fractures: a Comparison of Bi-planar Robot Navigation With Optoelectronic Navigation in a Synbone Hip Model Trial." *Chinese Medical Journal* 124(23) (2011): 3906-3911.

Yoshimitsu, K et al. "A Novel Four-wire-driven Robotic Catheter for Radio-frequency Ablation Treatment." *International Journal of Computer Assisted Radiology and Surgery* 9(5) (2014): 867-874.

Guo, J et al. "A novel robotic catheter system with force and visual feedback for vascular interventional surgery." *International Journal of Mechatronics and Automation* 2(1) (2012): 15-24.

European Office Action dated Apr. 28, 2021 issued in corresponding European Appln. No. 17176754.4.

\* cited by examiner

AUTONOMOUS CATHETERIZATION ASSEMBLY

PRIORITY STATEMENT

The present application hereby claims priority under 35 U.S.C. § 119 to European patent application number EP 17176754.4 filed Jun. 20, 2017, the entire contents of which are hereby incorporated herein by reference.

FIELD

At least one embodiment of the invention generally describes an autonomous catheterization assembly; a catheter arrangement of such a catheterization assembly; and/or a method of performing an autonomous catheterization procedure on a patient.

BACKGROUND

Catheterization is performed in a variety of medical situations for diagnostic and therapeutic procedures. Typically, during such a procedure, a skilled operator inserts a flexible hollow catheter into a major blood vessel at an entry point such as the femoral artery, and pushes the catheter along through the blood vessels of the vascular system until the target (e.g. an aneurysm, a blood clot, etc.) has been reached. Usually, the catheter encloses a thin and flexible guidewire which extends some small distance from the distal end of the catheter. The thin guidewire acts to assist the wider catheter in bending to follow a tortuous path through the vascular system. The tip of the catheter can be guided through a curved vessel or into the lumen of a branching vessel when gently pushed and/or rotated by the operator. Great care must be taken when manipulating the flexible end of the guidewire to ensure that blood vessels are not damaged or even ruptured. To assist the operator, images of the vascular system, for example angiograms, can be made at several critical stages during the procedure.

Catheterization procedures are particularly relevant for conditions such as embolism and arterial thrombosis, which can lead to ischaemia and irreversible tissue damage. In some cases, a mechanical embolectomy/thrombectomy is the only possible treatment to deal with the cause of the embolism and to restore blood flow. However, successful treatment of such conditions depends largely on the whether the patient has access to a skilled medical practitioner within the very short time window, which may be less than an hour by the time a diagnosis has been made. The clinical outcome of ischaemic stroke can only be improved by prompt diagnosis and early administration of a clot-busting drug or mechanical thrombectomy in case of a large vessel occlusion. The initiation of treatment is time-critical and any delay is associated with a worsening of the patient's recovery chances.

Due to various factors such as greater life expectancy, the incidence of stroke is rising in low and middle income countries (LMIC). Particularly in remote rural areas (also in high income countries), there is a lack of specialists that can perform state-of-the-art diagnostic examinations, make reliable decisions and carry out the necessary treatment. Without the possibility of treatment, a stroke patient may suffer debilitating damage. In LMIC countries in particular, the lack of optimized treatment results in an increase in the number of patients that are disabled following a stroke. The costs of providing care and the costs related to loss of productivity mean that the higher rate of stroke will become a significant socio-economic burden for LMIC countries in the near future. Even in industrialized countries, specialists with the required experience are not always available in rural hospitals. At best, stroke patients can be transferred to the closest stroke centre (if there is one within a reasonable radius), but such transfers result in delays and a worsening of the patient's recovery chances.

SUMMARY

At least one embodiment of the invention provides the system/method of performing a catheterization procedure that overcomes at least one of the problems mentioned above.

At least one embodiment is directed to an autonomous catheterization assembly; at least one embodiment is directed to a catheter arrangement; and at least one embodiment is directed to a method of performing an autonomous catheterization procedure on a patient.

According to at least one embodiment of the invention, the autonomous catheterization assembly comprises a catheter arrangement for insertion into the vascular system of a patient; a propulsion assembly adapted to propel elements of the catheter arrangement through the vascular system of a patient; a route computation module realized to compute a route through the vascular system to a target; and a control unit realized to actuate the propulsion assembly on the basis of the computed route and/or in response to a sensed condition in the interior of a vessel of the vascular system.

The catheter arrangement of at least one embodiment of the autonomous catheterization assembly comprises a sensor arrangement adapted to sense a condition in the interior of a vessel of the vascular system; a shape adjustment device arranged in a distal portion of the catheter arrangement, and an actuator arrangement realised to control the shape adjustment device to adjust the shape and/or orientation of the distal portion of the catheter arrangement.

According to at least one embodiment of the invention, the method of performing an autonomous catheterization procedure on a patient comprises the steps of providing such an autonomous catheterization assembly and connecting the catheter arrangement to the vascular system of the patient; providing image data to the route computation module of the catheterization assembly; initiating handover to the control unit of the catheterization assembly; and removing the catheterization assembly after completion of the catheterization procedure.

At least one embodiment of the invention is also directed to a non-transitory computer program product with a computer program that is directly loadable into the memory of a control unit of a catheterization assembly, and which comprises program code segments to perform the steps of at least one embodiment of the inventive method when the program is executed by the control unit. In addition to the computer program, such a computer program product can also comprise further parts such as documentation and/or additional components, also hardware components such as a hardware key (dongle etc.) to facilitate access to the software.

A non-transitory computer readable medium such as a memory stick, a hard-disk or other transportable or permanently-installed carrier can serve to transport and/or to store the executable parts of the computer program product so that these can be read from a processor unit of the control unit of the catheterization assembly. A processor unit can

BRIEF DESCRIPTION OF THE DRAWINGS

Other objects and features of the present invention will become apparent from the following detailed descriptions

In the diagrams, like numbers refer to like objects throughout. Objects in the diagrams are not necessarily drawn to scale.

DETAILED DESCRIPTION OF THE EXAMPLE EMBODIMENTS

The drawings are to be regarded as being schematic representations and elements illustrated in the drawings are not necessarily shown to scale. Rather, the various elements are represented such that their function and general purpose become apparent to a person skilled in the art. Any connection or coupling between functional blocks, devices, components, or other physical or functional units shown in the drawings or described herein may also be implemented by an indirect connection or coupling. A coupling between components may also be established over a wireless connection. Functional blocks may be implemented in hardware, firmware, software, or a combination thereof.

Various example embodiments will now be described more fully with reference to the accompanying drawings in which only some example embodiments are shown. Specific structural and functional details disclosed herein are merely representative for purposes of describing example embodiments. Example embodiments, however, may be embodied in various different forms, and should not be construed as being limited to only the illustrated embodiments. Rather, the illustrated embodiments are provided as examples so that this disclosure will be thorough and complete, and will fully convey the concepts of this disclosure to those skilled in the art. Accordingly, known processes, elements, and techniques, may not be described with respect to some example embodiments. Unless otherwise noted, like reference characters denote like elements throughout the attached drawings and written description, and thus descriptions will not be repeated. The present invention, however, may be embodied in many alternate forms and should not be construed as limited to only the example embodiments set forth herein.

It will be understood that, although the terms first, second, etc. may be used herein to describe various elements, components, regions, layers, and/or sections, these elements, components, regions, layers, and/or sections, should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items. The phrase "at least one of" has the same meaning as "and/or".

Spatially relative terms, such as "beneath," "below," "lower," "under," "above," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below," "beneath," or "under," other elements or features would then be oriented "above" the other elements or features. Thus, the example terms "below" and "under" may encompass both an orientation of above and below. The device may be otherwise oriented (rotated 90 degrees or at other orientations) and the spatially relative descriptors used herein interpreted accordingly. In addition, when an element is referred to as being "between" two elements, the element may be the only element between the two elements, or one or more other intervening elements may be present.

Spatial and functional relationships between elements (for example, between modules) are described using various terms, including "connected," "engaged," "interfaced," and "coupled." Unless explicitly described as being "direct," when a relationship between first and second elements is described in the above disclosure, that relationship encompasses a direct relationship where no other intervening elements are present between the first and second elements, and also an indirect relationship where one or more intervening elements are present (either spatially or functionally) between the first and second elements. In contrast, when an element is referred to as being "directly" connected, engaged, interfaced, or coupled to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Expressions such as "at least one of," when preceding a list of elements, modify the entire list of elements and do not modify the individual elements of the list. Also, the term "exemplary" is intended to refer to an example or illustration.

When an element is referred to as being "on," "connected to," "coupled to," or "adjacent to," another element, the element may be directly on, connected to, coupled to, or adjacent to, the other element, or one or more other intervening elements may be present. In contrast, when an element is referred to as being "directly on," "directly connected to," "directly coupled to," or "immediately adjacent to," another element there are no intervening elements present.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Before discussing example embodiments in more detail, it is noted that some example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order. Although the flowcharts describe the operations as sequential processes, many of the operations may be performed in parallel, concurrently or simultaneously. In addition, the order of operations may be re-arranged. The processes may be terminated when their operations are completed, but may also have additional steps not included in the figure. The processes may correspond to methods, functions, procedures, subroutines, subprograms, etc.

Specific structural and functional details disclosed herein are merely representative for purposes of describing example embodiments of the present invention. This invention may, however, be embodied in many alternate forms and should not be construed as limited to only the embodiments set forth herein.

Units and/or devices according to one or more example embodiments may be implemented using hardware, software, and/or a combination thereof. For example, hardware devices may be implemented using processing circuity such as, but not limited to, a processor, Central Processing Unit (CPU), a controller, an arithmetic logic unit (ALU), a digital signal processor, a microcomputer, a field programmable gate array (FPGA), a System-on-Chip (SoC), a programmable logic unit, a microprocessor, or any other device capable of responding to and executing instructions in a defined manner. Portions of the example embodiments and corresponding detailed description may be presented in terms of software, or algorithms and symbolic representations of operation on data bits within a computer memory. These descriptions and representations are the ones by which those of ordinary skill in the art effectively convey the substance of their work to others of ordinary skill in the art. An algorithm, as the term is used here, and as it is used generally, is conceived to be a selfconsistent sequence of steps leading to a desired result. The steps are those requiring physical manipulations of physical quantities. Usually, though not necessarily, these quantities take the form of optical, electrical, or magnetic signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise, or as is apparent from the discussion, terms such as "processing" or "computing" or "calculating" or "determining" of "displaying" or the like, refer to the action and processes of a computer system, or similar electronic computing device/ hardware, that manipulates and transforms data represented as physical, electronic quantities within the computer system's registers and memories into other data similarly represented as physical quantities within the computer system memories or registers or other such information storage, transmission or display devices.

In this application, including the definitions below, the term 'module' or the term 'controller' may be replaced with the term 'circuit.' The term 'module' may refer to, be part of, or include processor hardware (shared, dedicated, or group) that executes code and memory hardware (shared, dedicated, or group) that stores code executed by the processor hardware.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

Software may include a computer program, program code, instructions, or some combination thereof, for independently or collectively instructing or configuring a hardware device to operate as desired. The computer program and/or program code may include program or computer-readable instructions, software components, software modules, data files, data structures, and/or the like, capable of being implemented by one or more hardware devices, such as one or more of the hardware devices mentioned above. Examples of program code include both machine code produced by a compiler and higher level program code that is executed using an interpreter.

For example, when a hardware device is a computer processing device (e.g., a processor, Central Processing Unit (CPU), a controller, an arithmetic logic unit (ALU), a digital signal processor, a microcomputer, a microprocessor, etc.), the computer processing device may be configured to carry out program code by performing arithmetical, logical, and input/output operations, according to the program code. Once the program code is loaded into a computer processing device, the computer processing device may be programmed to perform the program code, thereby transforming the computer processing device into a special purpose computer processing device. In a more specific example, when the program code is loaded into a processor, the processor becomes programmed to perform the program code and operations corresponding thereto, thereby transforming the processor into a special purpose processor.

Software and/or data may be embodied permanently or temporarily in any type of machine, component, physical or virtual equipment, or computer storage medium or device, capable of providing instructions or data to, or being interpreted by, a hardware device. The software also may be distributed over network coupled computer systems so that the software is stored and executed in a distributed fashion.

In particular, for example, software and data may be stored by one or more computer readable recording mediums, including the tangible or non-transitory computer-readable storage media discussed herein.

Even further, any of the disclosed methods may be embodied in the form of a program or software. The program or software may be stored on a non-transitory computer readable medium and is adapted to perform any one of the aforementioned methods when run on a computer device (a device including a processor). Thus, the non-transitory, tangible computer readable medium, is adapted to store information and is adapted to interact with a data processing facility or computer device to execute the program of any of the above mentioned embodiments and/or to perform the method of any of the above mentioned embodiments.

Example embodiments may be described with reference to acts and symbolic representations of operations (e.g., in the form of flow charts, flow diagrams, data flow diagrams, structure diagrams, block diagrams, etc.) that may be implemented in conjunction with units and/or devices discussed in more detail below. Although discussed in a particularly manner, a function or operation specified in a specific block may be performed differently from the flow specified in a flowchart, flow diagram, etc. For example, functions or operations illustrated as being performed serially in two consecutive blocks may actually be performed simultaneously, or in some cases be performed in reverse order.

According to one or more example embodiments, computer processing devices may be described as including various functional units that perform various operations and/or functions to increase the clarity of the description. However, computer processing devices are not intended to be limited to these functional units. For example, in one or more example embodiments, the various operations and/or functions of the functional units may be performed by other ones of the functional units. Further, the computer processing devices may perform the operations and/or functions of the various functional units without sub-dividing the operations and/or functions of the computer processing units into these various functional units.

Units and/or devices according to one or more example embodiments may also include one or more storage devices. The one or more storage devices may be tangible or non-transitory computer-readable storage media, such as random access memory (RAM), read only memory (ROM), a permanent mass storage device (such as a disk drive), solid state (e.g., NAND flash) device, and/or any other like data storage mechanism capable of storing and recording data. The one or more storage devices may be configured to store computer programs, program code, instructions, or some combination thereof, for one or more operating systems and/or for implementing the example embodiments described herein. The computer programs, program code, instructions, or some combination thereof, may also be loaded from a separate computer readable storage medium into the one or more storage devices and/or one or more computer processing devices using a drive mechanism. Such separate computer readable storage medium may include a Universal Serial Bus (USB) flash drive, a memory stick, a Blu-ray/DVD/CDROM drive, a memory card, and/or other like computer readable storage media. The computer programs, program code, instructions, or some combination thereof, may be loaded into the one or more storage devices and/or the one or more computer processing devices from a remote data storage device via a network interface, rather than via a local computer readable storage medium. Additionally, the computer programs, program code, instructions, or some combination thereof, may be loaded into the one or more storage devices and/or the one or more processors from a remote computing system that is configured to transfer and/or distribute the computer programs, program code, instructions, or some combination thereof, over a network. The remote computing system may transfer and/or distribute the computer programs, program code, instructions, or some combination thereof, via a wired interface, an air interface, and/or any other like medium.

The one or more hardware devices, the one or more storage devices, and/or the computer programs, program code, instructions, or some combination thereof, may be specially designed and constructed for the purposes of the example embodiments, or they may be known devices that are altered and/or modified for the purposes of example embodiments.

A hardware device, such as a computer processing device, may run an operating system (OS) and one or more software applications that run on the OS. The computer processing device also may access, store, manipulate, process, and create data in response to execution of the software. For simplicity, one or more example embodiments may be exemplified as a computer processing device or processor; however, one skilled in the art will appreciate that a hardware device may include multiple processing elements or processors and multiple types of processing elements or processors. For example, a hardware device may include multiple processors or a processor and a controller. In addition, other processing configurations are possible, such as parallel processors.

The computer programs include processor-executable instructions that are stored on at least one non-transitory computer-readable medium (memory). The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc. As such, the one or more processors may be configured to execute the processor executable instructions.

The computer programs may include: (i) descriptive text to be parsed, such as HTML (hypertext markup language) or XML (extensible markup language), (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Haskell, Go, SQL, R, Lisp, Java®, Fortran, Perl, Pascal, Curl, OCaml, Javascript®, HTML5, Ada, ASP (active server pages), PHP, Scala, Eiffel, Smalltalk, Erlang, Ruby, Flash®, Visual Basic®, Lua, and Python®.

Further, at least one embodiment of the invention relates to the non-transitory computer-readable storage medium including electronically readable control information (processor executable instructions) stored thereon, configured in such that when the storage medium is used in a controller of a device, at least one embodiment of the method may be carried out.

The computer readable medium or storage medium may be a built-in medium installed inside a computer device main body or a removable medium arranged so that it can be separated from the computer device main body. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The term code, as used above, may include software, firmware, and/or microcode, and may refer to programs, routines, functions, classes, data structures, and/or objects. Shared processor hardware encompasses a single microprocessor that executes some or all code from multiple modules. Group processor hardware encompasses a microprocessor that, in combination with additional microprocessors, executes some or all code from one or more modules. References to multiple microprocessors encompass multiple microprocessors on discrete dies, multiple microprocessors on a single die, multiple cores of a single microprocessor, multiple threads of a single microprocessor, or a combination of the above.

Shared memory hardware encompasses a single memory device that stores some or all code from multiple modules. Group memory hardware encompasses a memory device that, in combination with other memory devices, stores some or all code from one or more modules.

The term memory hardware is a subset of the term computer-readable medium. The term computer-readable medium, as used herein, does not encompass transitory electrical or electromagnetic signals propagating through a medium (such as on a carrier wave); the term computer-readable medium is therefore considered tangible and non-transitory. Non-limiting examples of the non-transitory computer-readable medium include, but are not limited to, rewriteable non-volatile memory devices (including, for example flash memory devices, erasable programmable read-only memory devices, or a mask read-only memory devices); volatile memory devices (including, for example static random access memory devices or a dynamic random access memory devices); magnetic storage media (including, for example an analog or digital magnetic tape or a hard disk drive); and optical storage media (including, for example a CD, a DVD, or a Blu-ray Disc). Examples of the media with a built-in rewriteable non-volatile memory, include but are not limited to memory cards; and media with a built-in ROM, including but not limited to ROM cassettes; etc. Furthermore, various information regarding stored images, for example, property information, may be stored in any other form, or it may be provided in other ways.

The apparatuses and methods described in this application may be partially or fully implemented by a special purpose computer created by configuring a general purpose computer to execute one or more particular functions embodied in computer programs. The functional blocks and flowchart elements described above serve as software specifications, which can be translated into the computer programs by the routine work of a skilled technician or programmer.

Although described with reference to specific examples and drawings, modifications, additions and substitutions of example embodiments may be variously made according to the description by those of ordinary skill in the art. For example, the described techniques may be performed in an order different with that of the methods described, and/or components such as the described system, architecture, devices, circuit, and the like, may be connected or combined to be different from the above-described methods, or results may be appropriately achieved by other components or equivalents.

According to at least one embodiment of the invention, the autonomous catheterization assembly comprises a catheter arrangement for insertion into the vascular system of a patient; a propulsion assembly adapted to propel elements of the catheter arrangement through the vascular system of a patient; a route computation module realized to compute a route through the vascular system to a target; and a control unit realized to actuate the propulsion assembly on the basis of the computed route and/or in response to a sensed condition in the interior of a vessel of the vascular system.

The catheter arrangement of at least one embodiment of the autonomous catheterization assembly comprises a sensor arrangement adapted to sense a condition in the interior of a vessel of the vascular system; a shape adjustment device arranged in a distal portion of the catheter arrangement, and an actuator arrangement realised to control the shape adjustment device to adjust the shape and/or orientation of the distal portion of the catheter arrangement.

In the autonomous catheterization assembly of the invention, navigation of the catheter arrangement through the patient's vascular system towards a target is based on a route or "vascular roadmap" calculated prior to the procedure. The roadmap may be derived from data sets originating from an angiography, computed tomography or MRI imaging procedure as will be explained below. Progress of the catheter arrangement elements can then be monitored and controlled on the basis of the roadmap, and may be assisted by input received from sensors of the sensor arrangement. The vascular roadmap may comprise a set of instructions to the control unit to actuate elements of the propulsion assembly accordingly in order to advance/retract an element of the catheter assembly and/or to initiate a shape adjustment of the guidewire tip.

The catheter arrangement may comprise a flexible tube that accommodates the guidewire. Alternatively, the catheter arrangement may comprise a system of concentric or "nested" flexible tubes with decreasing diameter, and the innermost tube may accommodate a guidewire. The materials used for the catheter arrangement are preferably chosen to allow smooth movement between the elements of the catheter arrangement. For example, the surfaces of a tube may be coated with a smooth material such as PTFE.

An advantage of the autonomous catheterization assembly according to an embodiment of the invention is that it is capable of acting in an essentially entirely independent manner. For this reason, the inventive catheterization assembly may be referred to in the following as a robotic catheterization system. The only manual intervention steps that are required are the inputting of available patient data (age, gender, clinical symptoms, medical history, laboratory values, etc.) via a user interface of the catheterization assembly or initiate transfer from any other information system like electronic patient chart; the placement of a lock at a suitable point of entry (femoral artery, carotid artery, etc.) prior to the catheterization procedure to connect the catheter arrangement to the patient; and the removal of the lock and closure of the point of entry by applying compression draping after completion of the catheterization procedure. A nurse may perform these steps. However, the physical presence of a skilled operator such as a stroke specialist is not necessary for the procedure, meaning that specialist treatment can be brought closer to a patient in a remote area. It is possible that the entire procedure is performed in a completely autonomous manner by the inventive robotic catheterization system. Equally, of course, elements of the inventive catheterization assembly can be controlled from a remote location such as a comprehensive stroke centre by a skilled operator.

Advantageously, at least one embodiment of the inventive method can be applied for a variety of intravascular procedures such as thrombectomy, revascularization in myocardial infarction or acute coronary syndrome, in any other embolic-induced conditions or for any kind of endovascular procedures (e.g. coiling of aneurysm). When the autonomous catheterization assembly is in use, sensor input from the sensor arrangement can be processed and analysed to optimize the positioning of the guidewire tip within a vessel, and to safely guide the catheter assembly through tortuous vascular structures to reach a target, for example a clot or thrombus in an intracranial vessel. Because the catheter arrangement can be guided and controlled autonomously on the basis of the roadmap and real-time sensor feedback, the number of angiographic image acquisition steps can be reduced, so that the radiation dose to the patient can be kept favourably low.

According to at least one embodiment of the invention, the catheter arrangement of such an autonomous catheterization assembly comprises a shape adjustment device adapted to adjust the shape and/or orientation of a distal portion of an element of the catheter arrangement; and an actuator arrangement realized to actuate the shape adjustment device in response to a sensed condition in the vascular system and/or in response to a control signal received by the actuator arrangement. The term "distal" is used in its accepted sense to refer to the foremost portion or region of an element of the catheter arrangement. As mentioned above, the catheter arrangement may comprise one or more elements, for example a flexible tube that accommodates a guidewire, a flexible outer tube that accommodates one or more flexible inner tubes, a combination of several flexible tubes as well as a guidewire, etc. The shape adjustment device and actuator arrangement can be incorporated in one or more of these elements. Depending on the embodiment of the catheter arrangement, a guidewire is not necessarily required.

According to at least one embodiment of the invention, the method of performing an autonomous catheterization procedure on a patient comprises the steps of providing such an autonomous catheterization assembly and connecting the catheter arrangement to the vascular system of the patient; providing image data to the route computation module of the catheterization assembly; initiating handover to the control unit of the catheterization assembly; and removing the catheterization assembly after completion of the catheterization procedure.

In the context of at least one embodiment of the invention, "handover" to the control unit of the robotic catheterization system is to be understood as a step of informing the control unit of the catheterization assembly that it may proceed to guide the catheter arrangement though the patient's vascular system. This handover may be performed by the nurse or other medical assistant that prepared the entry port, for example. Handover can be effected through a user interface, by selecting a command in a menu on a visual display, by pressing a specific button on a user interface, etc. Included in this process step is the definition of the starting point of the catheter/guidewire tip within the vascular system.

An advantage of at least one embodiment of the inventive method is that it can be performed in an essentially autonomous manner. The inventive method allows the high-end diagnosis and treatment of vascular disorders in remote areas or in any hospital or clinic that does not have a dedicated stroke/vascular facility. The inventive method may drastically improve the outlook for patients in remote areas, since resolving a thrombus is time-critical, especially in potentially life-threatening conditions like acute myocardial infarction or ischaemic stroke. The diagnosis and catheterization steps of the inventive method can be performed essentially entirely automatically, requiring only a minimal level of assistance by a nurse or similar; equally the procedure may be performed in a remote-control manner by a stroke/vascular expert at a remote location. By providing this level of high-end treatment to patients in remote areas, complication rates and cost of care can be favourably reduced. Another advantage of the invention is that it is not necessary for any nurse or physician to be in the same room as the patient while an X-ray angiogram is being obtained, so that the method can also advantageously reduce the radiation dose administered to personnel during such a catheterization procedure. Of course, radiation dose to the patient is also reduced, because the ability of the inventive robotic catheterization system to carry out a catheterization procedure in an essentially autonomous manner can significantly reduce the number of fluoroscopy imaging steps.

At least one embodiment of the invention is also directed to a non-transitory computer program product with a computer program that is directly loadable into the memory of a control unit of a catheterization assembly, and which comprises program code segments to perform the steps of at least one embodiment of the inventive method when the program is executed by the control unit. In addition to the computer program, such a computer program product can also comprise further parts such as documentation and/or additional components, also hardware components such as a hardware key (dongle etc.) to facilitate access to the software.

A non-transitory computer readable medium such as a memory stick, a hard-disk or other transportable or permanently-installed carrier can serve to transport and/or to store the executable parts of the computer program product so that these can be read from a processor unit of the control unit of the catheterization assembly. A processor unit can comprise one or more microprocessors or their equivalents.

Particularly advantageous embodiments and features of the invention are given by the claims, as revealed in the following description. Features of different claim categories may be combined as appropriate to give further embodiments not described herein.

As mentioned above, the inventive method can be used for intravascular procedures such as thrombectomy, interventional revascularization, any other embolic-induced conditions or endovascular procedures (e.g. aneurysm coiling). In the following, without restricting the invention in any way, it may be assumed that the catheterization procedure is a mechanical thrombectomy procedure. It may also be assumed that the vascular system is the circulatory system of the patient, and a vessel of the vascular system may be understood to be a blood vessel. The inventive catheterization assembly may therefore be understood to be realized to guide a catheter into a blood vessel such as a carotid or intracranial artery.

The catheter arrangement can comprise a catheter that is realized to accommodate a guidewire. In such an embodiment, the guidewire can be constructed to comprise the shape adjustment device at or near its distal end (or "tip") and the actuator arrangement that controls the shape adjustment device to adjust the shape and/or orientation of the distal end of the guidewire. Alternatively, the catheter arrangement does not use a guidewire, and may simply comprise a catheter that is constructed to comprise the shape adjustment device and the actuator arrangement in order to adjust the shape and/or orientation of the distal end of the catheter. In such an embodiment, shape/orientation adjustment can be achieved by incorporating miniaturized balloon-like elastic chambers and/or channels in the catheter walls at the distal end of the catheter, and selectively inflating/deflating these to effect a shape-change of the tip of the catheter. To this end, a suitable fluid such as saline might be used to fill the chambers. Of course, various combinations of these embodiments are possible, for example the catheter arrangement may comprise two (or more) nested catheters, whereby one of these (for example the innermost inner catheter) may comprise the shape adjustment device and actuator arrangement. An embodiment in which more than one element of the catheter arrangement can change the shape of its distal end is also possible, for example it would be conceivable that a guidewire as well as an enclosing catheter might be equipped with a shape adjustment device and a corresponding actuator arrangement.

In the following, but without restricting the invention in any way, it may be assumed that the catheter arrangement comprises a catheter and a guidewire, and that the guidewire is constructed to comprise the shape adjustment device and the actuator arrangement so that it can adjust the shape and/or orientation of its tip.

An advantage of such a guidewire is that a single guidewire can be used throughout a complete procedure. This contrasts favourably with the prior art methods, which require the provision of a wide selection of guidewires, each with a different combination of primary and secondary curves. The prior art approach requires that a skilled operator be able to select a suitable guidewire; to identify when the guidewire is unable to proceed further through the vascular system, to identify which alternative guidewire might be better; and to exchange the guidewires. The guidewire of the inventive catheter arrangement does not need to be changed, since it can adapt to essentially any change of direction within the vascular system, and does not need to be manufactured to have a predefined primary and secondary curve. Instead, the guidewire of the inventive catheter arrangement is constructed in such a way that it can alter the shape of its tip deliberately in response to an impulse. This internal or external impulse can originate from a controller of a catheterization procedure and may be issued in response to a signal, for example in response to a signal originating from a sensor of the sensor arrangement.

At least one embodiment of the inventive method of performing catheterization autonomously is preferably initiated following the results of an automated image evaluation step. For example, a 3D angiogram, a 3D CT angiogram or a 3D MR angiogram and/or perfusion images of the patient are acquired and are automatically evaluated to arrive at a diagnosis. Together with the vascular information derived from an angiogram, perfusion images may be helpful in identifying the best vascular route to the target. Alternatively or in addition, CT (computed tomograph) or MR (magnetic resonance) images may be obtained and evaluated. Preferably, any such images are generated using optimized protocols provided by the control unit. The control unit of the inventive catheterization assembly may also be realized to communicate directly with an imaging device such as a fluoroscopy system, a computed tomograph or a magnetic resonance imaging scanner, or may even incorporate such an imaging device.

A suitable diagnostic program then analyses the images. The diagnostic software can comprise any appropriate machine learning algorithm and computerized decision algorithm that have been trained using suitable training data sets such as brain atlases, for example. With the advances in neural networks and machine learning, such diagnostic software may be able to differentiate between brain haemorrhage, ischaemic infarction and other brain disorders with a very high degree of accuracy. The diagnostic software may be able to automatically identify and measure a thrombus, for example. Such an algorithm may be trained to check for indications and contraindications and to weight the available facts according to their relevance and to comparing the results with the outcome data of a cohort of patients exhibiting comparable parameters. If the diagnostic programme considers the likelihood for a positive outcome is high, it can notify the operator of the most suitable course of treatment. For example, in the case of a thromboembolism identified in a cranial vessel and after considering all the available facts in the light of statistical data, the diagnostic programme may decide that drug-induced thrombolysis may be insufficient, and that a mechanical thrombectomy would be necessary in order to completely remove the clot (thrombus).

In case indication for a mechanical thrombectomy is given, trained personnel will perform the necessary arterial puncture using a lock system, and will couple the robotic catheterization system to the lock. The robotic catheterization system proceeds to automatically advance the catheter assembly into the patient's vascular system. A "roadmap" or route to the target (thrombus) can be obtained in various ways.

In a preferred embodiment of the invention, a vascular roadmap is computed from one or more suitable images of the vascular system, for example from a 3D angiogram. The control unit can release a radio-opaque contrast agent into the patient's vascular system through the catheter assembly and then initiate the acquisition of an X-ray based angiogram. Alternatively or in addition, a CT-angiogram obtained prior to the procedure may be used. The route computation module computes a suitable roadmap on the basis of one or more such images and may also translate them into a patient-centred coordinate system used for navigation purposes.

The required movement of the catheter arrangement is determined by measuring the distances between branches of the vascular system and identifying the direction in which the guidewire tip must move whenever it reaches a "junction" in the roadmap. The roadmap may be updated at regular intervals during the procedure, for example in case the patient should shift his or her position even only slightly. The roadmap may also be updated or adjusted on the basis of the flow pressure and/or flow direction of the blood, which may be measured using one or more appropriate sensors arranged on the guidewire. A patient-centred coordinate system may be defined using an optical or infrared camera to identify reference points such as the position of the patient's head, the insertion point of the lock, etc. This information can be used to establish the patient-centric coordinate system. To reduce motion artefacts, the patient can rest on a vacuum mattress arranged on the table of an angiography suite. A radiopaque grid can be placed over the patient during scanning and fluoroscopy to facilitate detection of any movement of the patient and to determine any necessary adjustment of the coordinate system.

The shape adjustment device of the guidewire can be realised in any one of various ways. For example, the shape adjustment device may comprise a flexible section in a distal region of the guidewire, and an actuator that can force the flexible section to assume a desired shape and/or orientation. Such a flexible section can be realised as a coil in the distal portion of the guidewire, enclosed in a smooth cover such as a silicon cover. In another embodiment, the shape adjustment device may incorporate a series of jointed elements in the distal portion of the guidewire, and an actuator for bringing the series of jointed elements into a desired shape and/or orientation. Alternatively or in addition, a shape adjustment device may make use of a bimetallic device, a piezo-electric device, a hydrogel, a shape-memory alloy, a micro-electromechanical device, a tendon arrangement etc., to effect a bending of a flexible section of the guidewire. Preferably, the shape adjustment device is realized to change its shape based on a suitable stimulus such as a chemical reaction, a temperature change, an electrical field, a solvent, light, etc. For example, the distal region of the catheter wall may comprise an annular arrangement of several chambers, each containing a volume of a substance and each connected in some way to a stimulus source.

For example, if light is the stimulus, each chamber can be connected to the control unit over a light guide; if electricity is the stimulus, each chamber can be connected to the control unit over an electrical conductor, etc. In another approach, each chamber can be connected via a narrow duct to a fluid source, and the control unit can pump in or draw out fluid volume(s) as required to adjust the chamber sizes. The control unit may alter the stimulus as required to specifically change the viscosity and/or the volume of the substance in each chamber in order to achieve a desired expansion or retraction of the chambers. By appropriate control of the chamber volumes, the distal region of the catheter can be made to bend by a desired amount and in a desired direction.

The sensor arrangement can comprise any number of sensors that are capable of sensing a relevant condition inside a blood vessel. For example, a diagnostic catheterization procedure may be carried out to establish the degree of stenosis or even the total occlusion of a blood vessel. To this end, the sensor arrangement may comprise a suitable imaging sensor to capture images of the vessel lumen and the walls of a blood vessel.

An example of such an imaging sensor may be an optical coherence tomography (OCT) device. Such an imaging sensor can be used to assist the navigation and advancement of the guidewire. An imaging sensor may be arranged near the distal end of the catheter tube that encloses the guidewire, for example. Such an imaging sensor may also help to determine whether there are further atherosclerotic plaques or other relevant pathologies which may cause any problems in the future. Of course, an imaging device may be realised as an optical sensor. An illumination source for such an optical sensor may be realised using an LED arrangement.

Other sensors may be deployed to monitor the restoration of the blood flow; to measure the concentration of contrast agent using the knowledge that an occluded vessel has less washout; a sensor to measure fibrinogen, clot stickiness, D-dimer, hormone levels, contrast medium levels, etc. Alternatively or in addition, the sensor arrangement can comprise one or more pressure sensors arranged at the tip of a guidewire. A pressure sensor can be a strain gauge, a forcesensing resistor, or any other suitable type of sensor. Data from a pressure sensor can be analysed, for example, to detect the lumen of a branching vessel. Feedback from such a pressure sensor can also be used to ensure that the distal end of the catheter arrangement does not damage the vessel walls. Alternatively or in addition, a pressure sensor of the sensor arrangement may comprise a blood pressure transducer or haemodynamic monitor.

The catheter arrangement preferably comprises at least one tool adapted to perform a specific task inside a blood vessel. The types of tool that can be used to perform tasks inside a patient's vascular system will be known to the skilled person. For example, a tool arrangement may comprise an embolectomy tool for detaching an embolus from a blood vessel and/or a retriever tool realised to collect embolus material for removal from the patient. A stent retriever can be transported to the site of an embolism in order to open the obstructed vessel and to remove the clot. The outer catheter may also include a balloon, inflated with saline controlled by the control unit.

Moreover, permanent suction will be initiated by the control unit in order to support clot retrieval either in combination with a stent retriever or alone. Another type of tool can be used to coil an aneurysm, for example. A tool may be provided to allow direct intra-arterial application of medication, e.g. a drug to initiate embolization of a tumour-feeding artery in the case of interventional oncology.

Deployment of a tool such as a stent retriever is initiated on the basis of input received from the sensor arrangement as well as the position of the guidewire within the vascular system, calculated on the basis of the roadmap. Equipped with such a tool arrangement, the inventive catheterization assembly can be used in a method to perform a mechanical embolectomy procedure in a completely autonomous manner. For example, a vessel occlusion can be identified by the diagnostic software of the control unit; a route to that target is then computed by the route computation module using a 3D angiogram or other suitable image; the propulsion assembly is controlled to move the catheter and guidewire, whereby the guidewire "finds its way" into the correct blood vessels on the basis of the roadmap and sensor input; upon reaching the target, the catheter is moved forward in order to pierce the clot.

Prior to this step, other tasks like inflating a blocking balloon, continuous suction in order to support clot removal will be initiated by the control unit. Once the tip of the catheter reaches the end of the clot, a clot retriever is advanced automatically and opened by a signal issued by the control unit once it has reached it designated position. The readings from a suitable sensor such as a shear stress sensor can be analysed to determine whether the clot has been completely grabbed by the retriever. If this is the case, the retriever is folded and retracted (with the clot) into the catheter.

The control unit is realized to monitor the progress of the catheter assembly by tracking the position of the guidewire tip relative to the roadmap (for example by way of a fluoroscopy marker at the distal end of the catheter), and to issue control signals that adjust the guidewire tip to make it (and the catheter) safely pass through the vascular system to advance towards the target. To advance the catheter arrangement through the vascular system, the propulsion assembly preferably comprises a device of gripping the guidewire and moving it further into the vascular system. This can be achieved using a suitable pressurized air system, for example.

In a preferred embodiment of the invention, the propulsion assembly comprises a pair of rubber-coated wheels to simultaneously grip the guidewire while pushing it gently further into the vascular system (or retracting it). Such an assembly can also be realized to effect a rotatory movement of the guidewire about its length. Any slight rotation of the guidewire at its base will propagate to the tip, and the tip will therefore also rotate slightly. In this way, the guidewire tip can be brought into a suitable orientation, for example to face into the lumen of a branching vessel. The propulsion assembly preferably comprises a similar device(s) for advancing the catheter, for example several rubber-coated wheels arranged to simultaneously grip the catheter while pushing it gently further into the vascular system (or retracting it). Preferably, a device for displacing the guidewire is controllable independently of a device for displacing the catheter, so that the catheter and guidewire can be advanced/retracted separately or together as the situation arises.

At any time, it is advantageous for at least one embodiment of the inventive catheterization assembly to know the precise location of the distal end of the catheter assembly. In one approach, the location of the distal end can be determined using data from sensors of the sensor arrangement. For example, image data from an imaging sensor could be continually analysed to track the progress of the distal end through the vessel tree.

Alternatively or in addition, the distal end position in the vessel tree might be determined using additional angiograms and related to the patient-centred coordinate system as described above. In a preferred embodiment of the invention, the catheterization assembly comprises a distance tracker that is capable of tracking the distances traveled by the elements of the catheter arrangement along the computed route in the patient's vascular system.

This information can be used to accurately estimate the position of the guidewire tip in the vascular system and relative to the target being approached by the guidewire. For example, a distance tracker can be realised by providing a device for counting the rotations of a wheel of the propulsion assembly whenever it advances the guidewire (or catheter) further into the vascular system. A high level of accuracy for such a distance tracker can be achieved by realizing it to track even very small displacements, for example displacements corresponding to only a few degrees of rotation of a gripping wheel. The position of the catheter assembly distal end as determined by such a distance tracker may be compared to its position as seen in an angiogram taken during the procedure.

Information collected by the distance tracker can be used in controlling the propulsion assembly. For example, the distance tracker can be used to monitor the distance traveled from a specific "junction" in the vascular roadmap. As soon as the required distance has been traveled to the next junction or branch, a step of bending and rotating the guidewire tip can be carried out in order to point the guidewire tip into the right direction for entering the lumen of the blood vessel at the next branch. The degree of rotation is also measured, for example by tracking the number of rotations of a rotatory actuator of the propulsion assembly.

In a preferred embodiment of the invention, the catheterization assembly comprises a communication device for exchanging data and/or control signals between the control unit and any actuator, tool or sensor of the catheter arrangement. Such a communication device might comprise an electrical conductor arranged inside the guidewire to transmit control signals to actuators of the shape adjustment device; an electrical conductor arranged inside the guidewire or inside a tube of the catheter arrangement to transmit data from a sensor to the control unit, etc. In this way, for example, a flow sensor may report sensed flow values to the control system at regular intervals.

When the target is an embolus or other occlusion, the blood flow will reduce significantly as the guidewire tip approaches the target. By analysing the data in the context of the computed route, the control system may use the information to determine when the guidewire tip has reached the target. Data provided by a flow sensor may also be evaluated to determine the extent of reperfusion after a clot has been removed.

In a preferred embodiment of the invention, the control unit is realised to deploy a tool in a certain situation, for example on the basis of the diagnosis and/or in response to a condition sensed by the sensor arrangement. For example, when a thrombus has been reached by the catheter arrangement, the control unit initiates retraction of the guidewire, followed by the insertion of a retrieval system into the catheter, and then instructs the displacement assembly to advance the retrieval system towards the clot. The control unit is also capable of identifying the position of the clot retriever inside the thrombus, and whether the thrombus has been traversed. At that point in time, the control unit can initiate suction, opening of a stent and can evaluate (e.g. using a signal obtained from a shear stress sensor) whether the clot has been captured.

Before retraction of the catheter arrangement, the control unit may automatically initiate a perfusion imaging step (including the automatic administration of a contrast agent) and evaluation by a computerized algorithm of the control unit in order to document and evaluate the radiological outcome of the procedure. If the assessment is positive, the catheter assembly is automatically withdrawn from the patient's vascular system (along with the captured thrombus). In the case of a negative assessment, the procedure may be automatically initiated again. Should the control unit consider the procedure to be complete, it instructs the propulsion assembly to retract the catheter arrangement.

In a preferred embodiment of the invention, the control unit of the catheterization assembly is realised to release a contrast agent into the vascular system through the catheter arrangement. Once the catheter has advanced as far as the internal carotid artery, for example, a contrast bolus can be released, and a 3D angiography procedure can be initiated if it is still necessary to more precisely identify the vessel occluded by the clot.

If the catheter system is in place, proximal balloon blockage of the vessel in order to facilitate clot retrieval and avoid dispersion of clot fragments along the blood flow will be initiated by the control unit.

Figure 1:
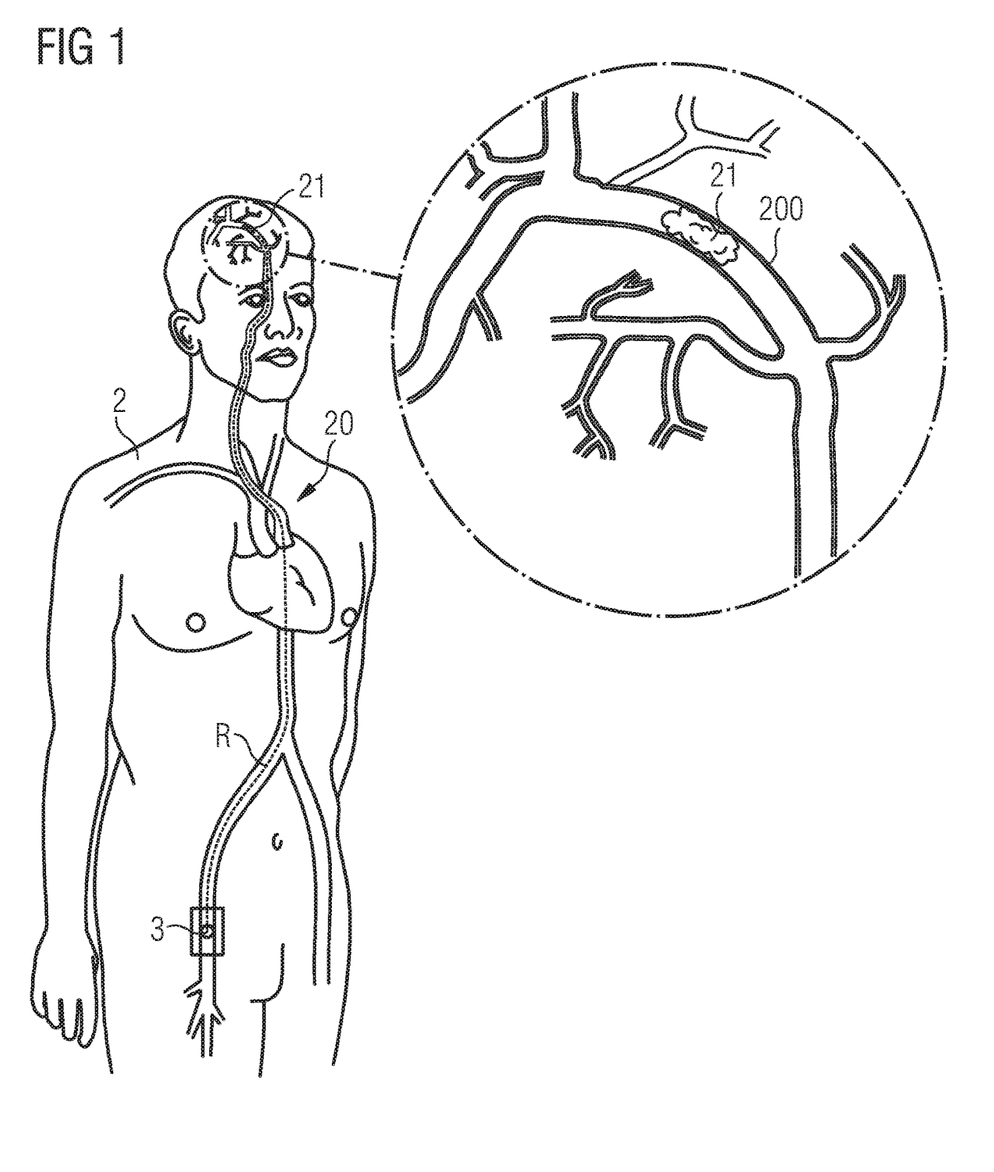
FIG. 1 shows a simplified schematic drawing of the vascular system of a patient.

FIG. 1 is a simplified schematic drawing of a patient 2, indicating the vascular system 20 with the heart and some of the relevant arteries of the vessel tree. An embolus 21 is indicated in a cranial vessel of the patient's brain (seen more clearly in the enlarged part of the drawing). To reach such an embolus in order to perform thrombolysis or a thrombectomy, a catheterization procedure is generally carried out. To this end, a lock system 3 or port is prepared at a suitable point of entry, for example into the femoral artery in the groin area. In a prior art method, a skilled practitioner selects an appropriate guidewire on the basis of his experience, inserts a catheter through the port, and inserts the selected guidewire into the catheter. If necessary, the practitioner may need to exchange the guidewire for a more suitable one if the originally selected guidewire is unable to be moved into a branch of the vascular system.

To guide the catheter assembly (catheter and guidewire) to the target, the practitioner performing the procedure must have detailed knowledge of the internal anatomy and must be familiar with the capabilities and behaviour of the catheter arrangement. The practitioner may plan the procedure with the help of angiogram images obtained in advance, and will generally also consult further images such as fluoroscopy images, X-ray images etc. obtained during the procedure in order to assess the progress of the catheter and guidewire.

A main drawback of the prior art approach is that the presence of a skilled practitioner is required to perform an accurate diagnosis as well as to carry out the procedure. However, in low middle income countries, there may not be any such skilled practitioner available within a practicable radius, so that a thrombosis patient may not be able to be treated within the relatively small time window.

A further drawback of the prior art approach is that the practitioner may be exposed to radiation doses if X-ray imaging needs to be performed during such a procedure in order to monitor the progress of a manually advanced guidewire and catheter arrangement. While the doses during a single procedure can be relatively small, accumulation of such doses over time can be problematic, at least for the practitioner.

The method according to an embodiment of the invention can overcome these problems by using an autonomous catheterization apparatus. Instead of requiring a skilled practitioner to manipulate the catheter and guidewire to an embolus or other target, the inventive catheterization apparatus computes a "vascular roadmap" or route R through the patient's vascular system 20 from a point of entry 3 to the target 21. The vascular roadmap R is preferably computed in advance, using one or more 3D-angiograms of the patient's vascular system. The route R can be computed from one or more images (e.g. angiograms) obtained in advance of the procedure (before the catheterization has commenced) or during the procedure (after the catheterization has commenced). For example, a route or roadmap can comprise a set of instructions to the control unit, which actuates the propulsion assembly accordingly to advance/retract an element of the catheter assembly and/or to initiate an adjustment of the guidewire tip. Moreover, the route computation module generating the roadmap may also calculate the diameter of the smallest vessel and suggest the maximum size of the outermost tube of the catheter arrangement.

Figure 2:
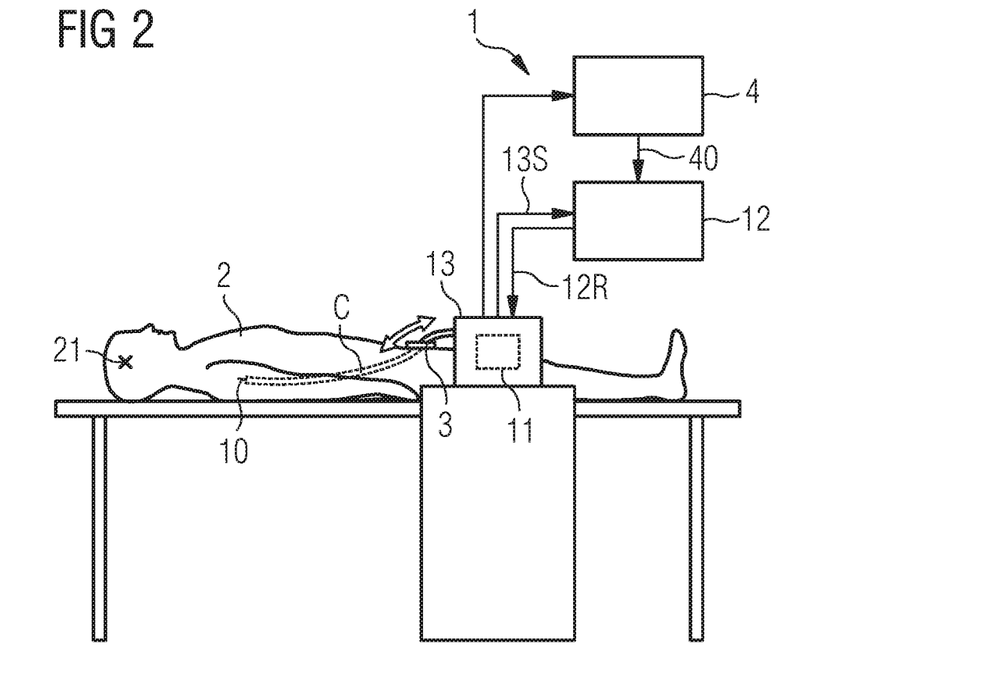
FIG. 2 is a schematic representation of a stage during a catheterization procedure performed using an embodiment of the inventive method.

FIG. 2 is a schematic representation of an embodiment of the inventive method. A patient 2 has been prepared for a catheterization procedure. This may only require that a nurse or other operator prepare a port 3 through which a catheter can be introduced into the patient's vascular system. An embodiment of the inventive catheterization assembly 1 is in place, showing that the catheter C is already proceeding along the route R indicated in FIG. 1. The route R has been previously computed by a route computation module 12. To this end, image data 40 such as one or more angiograms may be obtained from an imaging device 4 prior to the procedure, and if necessary also during the procedure. Relevant route data 12R are provided to a control unit 13, which controls a propulsion assembly 11 on the basis of the computed route R. The route data 12R may be understood as a set of motion primitives or navigation instructions based on the vascular roadmap. A motion primitive may be understood as a directive such as "forward", "backward", "rotate", "bend" and may be accompanied by one or more parameters such as the distance to move, the number of degrees by which to bend or rotate, etc.

A motion primitive will generally describe a motion based on the momentary or current location of the distal end of the catheter assembly inside the patient's vascular system. The instructions can indicate, for example, that the distal end is to move slightly forward while bending by a certain amount and rotating by a certain amount in order to enter a specific vessel along the route, for example. The propulsion assembly 11 is realized to gently push and rotate the guidewire 10 and inner/outer tube C of the catheter arrangement into the vascular system. Route corrections or adjustments can be made on the basis of data 13S received from a sensor of the catheter arrangement, as will be explained below.

Equally, the propulsion assembly 11 may respond to data 13S received from a sensor in the guidewire 10, so that the guidewire 10 (and catheter C) proceed gently but efficiently along the computed route towards the target 21. During a catheterization procedure, the patient may be conscious and may shift his or her position during the procedure. Therefore, the route R should be updated at regular intervals, e.g. every few milliseconds using information from additional angiograms, from a sonar assembly, using feedback from the sensor arrangement, etc. A sonar arrangement can be based on ultrasound, for example. Alternatively, the loudness of acoustic signals originating from the heart can be analysed to determine the direction in which the guidewire tip is travelling. Evaluation of such additional data can assist in updating the roadmap and/or the navigation instructions.

Figure 3:
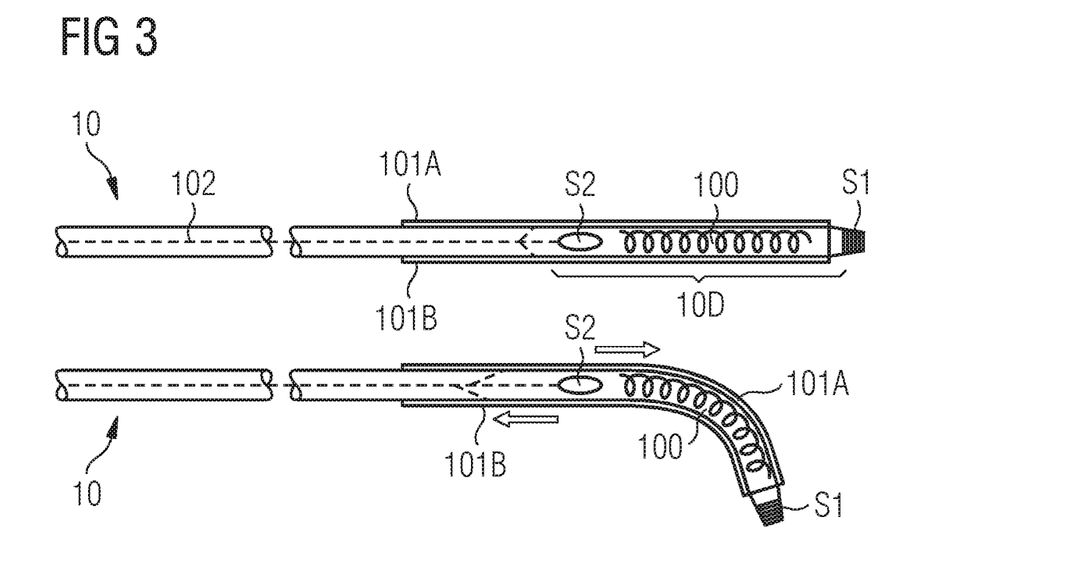
FIG. 3 shows an example embodiment of the inventive guidewire.

FIG. 3 shows an example embodiment of a guidewire 10 of the inventive catheter arrangement. The guidewire 10 has a small diameter (for example only a few mm) so that it can be inserted into a narrow-bore catheter tube to travel along the vascular system. A tool such as a stent, clot retriever etc., may be transported by the catheter tube in a manner that will be known to the skilled person.

The guidewire 10 has a sensor arrangement, in this case the example sensor arrangement comprises a pressure sensor S1 at the tip of the guidewire 10, and a blood flow sensor S2 arranged further inward along the distal end of the guidewire 10. The pressure sensor S1 can "feel" its way about the interior of a blood vessel to detect the lumen of a branching vessel, for example. When the propulsion assembly 11 is feeding the guidewire 10 into the vascular system to follow the roadmap, information from the pressure sensor S1 can be sent from the sensor S1 to the control unit 13, where it can be analysed to determine, for example, whether or not the guidewire should enter a detected branch vessel. To enter a detected branch vessel, the shape of the distal portion 10D of the guidewire 10 can be altered.

In this example embodiment, the shape adjustment device of the guidewire 10 comprises a flexible section 10D in the distal region of the guidewire 10, and a number of actuators 101A, 101B are arranged along the sides of the guidewire 10 to manipulate the flexible section 10D. As mentioned above, an actuator can be realized using a shape-memory alloy, a microelectromechanical system, a hydrogel, etc. Here, in response to a signal from the pressure sensor S1, one actuator 101A may extend while another actuator 101B may contract. As a result, the shape of the flexible distal portion 10D of the guidewire 10 will change. This can allow the tip of the guidewire 10 to enter the lumen of a detected branching vessel, for example.

In addition to or as an alternative to the rotatable gripper wheels described above, the propulsion assembly may avail of miniature pressurized tubes inside the walls of a catheter tube in order to advance the tube through the vascular system.

Figure 4:
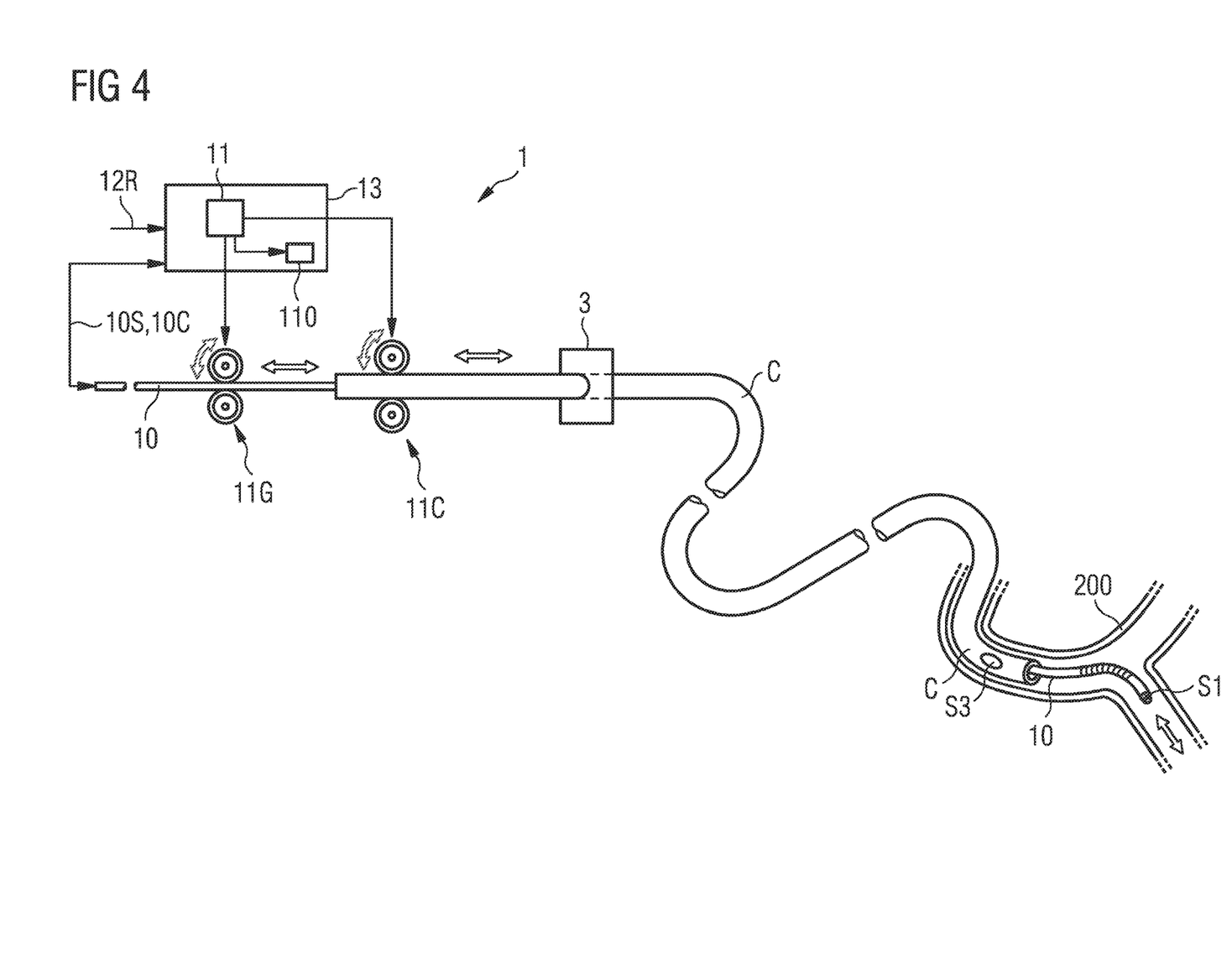
FIG. 4 shows parts of an embodiment of the inventive catheterization assembly.

FIG. 4 shows parts of an embodiment of the inventive catheterization assembly 1. The diagram shows the catheter arrangement, comprising a catheter C and an embodiment of the inventive guidewire 10. In this embodiment, in addition to a pressure sensor S1 and a flow sensor (not shown) arranged at the distal portion of the guidewire 10, a sensor S3 is shown at the distal end of the catheter tube C. The sensor can be an imaging sensor, for example.

A point of entry 3 is indicated schematically, and may be a port to the femoral artery as described above. The diagram also schematically indicates rotatory gripping assemblies 11C, 11G of the propulsion assembly 11 for advancing and retracting the catheter arrangement C, 10 through the vascular system of a patient. In this embodiment, the propulsion assembly 11 can comprise a first rotatory gripping assembly 11C for gripping and displacing the catheter C, and a second rotatory gripping assembly 11G for gripping and displacing the guidewire 10. If the catheter is realised as an outer tube enclosing an inner tube, separate rotatory gripping assemblies can be used to independently advance/retract the inner and outer catheter tubes. The control unit 13 of the catheterization assembly 1 can instruct the propulsion assembly 11 to separately control the rate of rotation and direction of rotation of each independent rotatory gripping assembly 11G, 11C in response to instructions or route data 12R received from the route computation module 12.

Distance trackers of the propulsion assembly 11 can be deployed as appropriate to monitor the distance traveled by the distal end of the guidewire 10 or catheter tube C. Data 10S received from a sensor S1, S2, S3 at the distal portion of the guidewire 10 can also be used by the control unit 13 to respond to a condition sensed at the tip of the guidewire 10. In this example embodiment, a sensor S1, S2, S3 can be electrically connected to the control unit 13 by conductors extending through the length of the guidewire 10. In the case that a sensor is an imaging sensor, for example the imaging sensor S3 in this example embodiment, data from such a sensor can be forwarded to the route computation model 12 for analysis, for example to assist in precisely tracking the position of the distal end in the vessel tree of the patient's vascular system.

Although the present invention has been disclosed in the form of example embodiments and variations thereon, it will be understood that numerous additional modifications and variations could be made thereto without departing from the scope of the invention. For example, the autonomous catheterization assembly may avail of a centerline navigation in which the propulsion assembly uses a jet of fluid to advance an element of the catheter arrangement. For example, a propulsion unit realised to suck in and expel a fluid such as blood, a saline solution etc., may be arranged near the distal end of the guidewire and may be realized to adapt its circumference to a reduction in the lumen of a vessel. While the inventive autonomous catheterization assembly has been described mainly in the context of performing tasks in the blood vascular system, it may of course find use in other parts of the body such as the gastrointestinal system (including the hepatobiliary system) or in cerebrospinal fluid chambers (ventricular system) of the brain.

For the sake of clarity, it is to be understood that the use of "a" or "an" throughout this application does not exclude a plurality, and "comprising" does not exclude other steps or elements. The mention of a "unit" or a "module" does not preclude the use of more than one unit or module.

The patent claims of the application are formulation proposals without prejudice for obtaining more extensive patent protection. The applicant reserves the right to claim even further combinations of features previously disclosed only in the description and/or drawings.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

None of the elements recited in the claims are intended to be a means-plus-function element within the meaning of 35 U.S.C. § 112(f) unless an element is expressly recited using the phrase "means for" or, in the case of a method claim, using the phrases "operation for" or "step for."

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An autonomous catheterization assembly, comprising:
    a catheter arrangement configured to be inserted into a vascular system of a patient, the catheter arrangement including
        a sensor arrangement configured to sense a condition in an interior of a vessel of the vascular system,
        a shape adjustment device in a distal portion of the catheter arrangement, and
        an actuator arrangement configured to control the shape adjustment device to adjust at least one of a shape or an orientation of the distal portion of the catheter arrangement;
    a propulsion assembly configured to propel elements of the catheter arrangement through the vascular system of the patient;
    processing circuitry configured to compute a route from a point of entry of the catheter arrangement through the vascular system to a target; and
    a control unit configured to actuate the propulsion assembly at least one of based upon the computed route or in response to a sensed condition in the interior of the vessel of the vascular system.

2. The autonomous catheterization assembly of claim 1, wherein the propulsion assembly is configured to advance and retract one element of the catheter arrangement, independently of other elements of the catheter arrangement.

3. The autonomous catheterization assembly of claim 2, further comprising:
    a distance tracker configured to track a distance travelled by an element of the catheter arrangement along the computed route.

4. The autonomous catheterization assembly of claim 2, wherein the sensor arrangement includes at least one of
- a pressure sensor,
- an imaging device to capture images of the interior of the vessel, or
- a blood pressure transducer.

5. The autonomous catheterization assembly of claim 2, wherein the catheter arrangement is configured to transport at least one tool for performing a specific task inside the vascular system.

6. The autonomous catheterization assembly of claim 5, wherein the at least one tool comprises at least one of
- an embolectomy tool configured to detach an embolus from the vessel, or
- a retriever tool configured to collect embolus material for removal from the patient.

7. The autonomous catheterization assembly of claim 1, further comprising:
- a distance tracker configured to track a distance travelled by an element of the catheter arrangement along the computed route.

8. The autonomous catheterization assembly of claim 1, wherein the sensor arrangement includes at least one of
- a pressure sensor,
- an imaging device to capture images of the interior of the vessel, or
- a blood pressure transducer.

9. The autonomous catheterization assembly of claim 1, wherein the catheter arrangement is configured to transport at least one tool for performing a specific task inside the vascular system.

10. The autonomous catheterization assembly of claim 9, wherein the at least one tool comprises at least one of
- an embolectomy tool configured to detach an embolus from the vessel, or
- a retriever tool configured to collect embolus material for removal from the patient.

11. The autonomous catheterization assembly of claim 9, wherein the control unit is configured to deploy the at least one tool of the catheter arrangement at least one of
- based upon a diagnosis, or
- in response to a condition sensed by the sensor arrangement.

12. The autonomous catheterization assembly of claim 1, wherein the catheter arrangement includes
- a catheter configured to accommodate a guidewire including the shape adjustment device; and
- the actuator arrangement.

* * * * *